US010286147B2

(12) United States Patent
Jang

(10) Patent No.: US 10,286,147 B2
(45) Date of Patent: May 14, 2019

(54) INTRAVENOUS FLUID SUPPLY DEVICE

(71) Applicant: Kwan Soon Jang, Gwacheon-si (KR)

(72) Inventor: Kwan Soon Jang, Gwacheon-si (KR)

(*) Notice: Subject to any disclaimer, the term of this patent is extended or adjusted under 35 U.S.C. 154(b) by 643 days.

(21) Appl. No.: 14/901,430

(22) PCT Filed: May 23, 2014

(86) PCT No.: PCT/KR2014/004642
§ 371 (c)(1),
(2) Date: Dec. 28, 2015

(87) PCT Pub. No.: WO2014/208895
PCT Pub. Date: Dec. 31, 2014

(65) Prior Publication Data
US 2016/0243303 A1 Aug. 25, 2016

(30) Foreign Application Priority Data

Jun. 27, 2013 (KR) .................. 10-2013-0074591

(51) Int. Cl.
*A61M 5/168* (2006.01)
*A61M 5/36* (2006.01)
(Continued)

(52) U.S. Cl.
CPC ........ *A61M 5/16813* (2013.01); *A61M 5/142* (2013.01); *A61M 5/162* (2013.01);
(Continued)

(58) Field of Classification Search
CPC ............ A61M 39/281; A61M 2205/11; A61M 2205/121; A61M 2205/12
See application file for complete search history.

(56) References Cited

U.S. PATENT DOCUMENTS 4,728,265 A * 3/1988 Cannon ............. A61M 5/14228
16/225
5,681,284 A * 10/1997 Herskowitz ......... A61M 5/1483
604/141
(Continued)

FOREIGN PATENT DOCUMENTS

JP 2001-025505 A 1/2001
JP 2001-523995 A 11/2001
(Continued)

*Primary Examiner* — Kami A Bosworth
*Assistant Examiner* — Alexandra Lalonde
(74) *Attorney, Agent, or Firm* — Novick, Kim & Lee, PLLC; Jae Youn Kim

(57) ABSTRACT

Provided is an intravenous fluid supply device that automatically extrudes and injects a predetermined amount of an infusion fluid at regular time intervals in a manipulated manner, regardless of the position of an infusion bag, using a microprocessor technology. The intravenous fluid supply device includes an extrusion means and a control means. The control means includes: an input means that sets an extrusion repetition cycle of the motor and a total amount of injection; a detection means that detects a top dead center of a motor fixing plate; a motor driving means that activates the motor; a microcontroller that controls the motor driving means according to a detection result of the detection means; and an LED lighting means that allows for monitoring of the flow of the infusion fluid according to the control of the microcontroller.

10 Claims, 20 Drawing Sheets

(51) Int. Cl.
*A61M 5/142* (2006.01)
*A61M 5/162* (2006.01)
*A61M 39/22* (2006.01)
*A61M 5/14* (2006.01)
*A61M 5/40* (2006.01)
*A61M 39/24* (2006.01)
*A61M 5/172* (2006.01)

(52) U.S. Cl.
CPC ...... *A61M 5/1684* (2013.01); *A61M 5/16809* (2013.01); *A61M 5/16886* (2013.01); *A61M 5/36* (2013.01); *A61M 5/365* (2013.01); *A61M 39/227* (2013.01); *A61M 5/1414* (2013.01); *A61M 5/172* (2013.01); *A61M 5/40* (2013.01); *A61M 39/24* (2013.01); *A61M 2005/14208* (2013.01); *A61M 2205/18* (2013.01); *A61M 2205/3306* (2013.01); *A61M 2205/3317* (2013.01); *A61M 2205/3375* (2013.01); *A61M 2205/50* (2013.01); *A61M 2205/502* (2013.01); *A61M 2205/52* (2013.01); *A61M 2205/581* (2013.01); *A61M 2205/8206* (2013.01); *A61M 2205/8212* (2013.01)

(56) References Cited

U.S. PATENT DOCUMENTS

| 6,261,262 | B1 | 7/2001 | Briggs et al. | |
| 6,491,659 | B1* | 12/2002 | Miyamoto | A61M 5/1689 604/30 |
| 2002/0115965 | A1* | 8/2002 | Jang | A61M 5/40 604/254 |
| 2006/0030836 | A1* | 2/2006 | Lee | A61M 5/14228 604/890.1 |
| 2006/0253064 | A1* | 11/2006 | Gelfand | A61B 5/201 604/31 |
| 2009/0204078 | A1* | 8/2009 | Mitchell | A61M 39/223 604/246 |

FOREIGN PATENT DOCUMENTS

| KR | 10-2003-0020254 A | 3/2003 |
| KR | 10-2006-0035131 A | 4/2006 |

* cited by examiner (a)

(b)

INTRAVENOUS FLUID SUPPLY DEVICE

CROSS-REFERENCE TO RELATED APPLICATIONS

This is the National Stage filing under 35 U.S.C. 371 of the International Application PCT/KR2014/004642 filed May 23, 2014, which claims priority under 35 U.S.C. 119 (a-d) to KR10-2013-0074951filed Jun. 27, 2013.

TECHNICAL FIELD

The present invention relates to an intravenous fluid supply device that extrudes and injects a predetermined amount of an infusion fluid at regular time intervals in a manipulated manner, regardless of the position of an infusion bag.

More particularly, the present invention relates to an intravenous fluid supply device that supplies a predetermined amount of an infusion fluid at regular time intervals by installing a suction check valve and an extrusion check valve in an elastic tube and pressing a portion of the elastic tube between the suction check valve and the extrusion check valve with a protruding portion of a motor fixing plate, which is different from a conventional infusion fluid injection method that requires an infusion bag to be placed e higher than the part of a human body to which an infusion fluid is injected and that requires an operator to use his or her senses to directly control the flow rate of an infusion fluid using a roller clamp-type infusion fluid control device or a complex mechanical device.

BACKGROUND ART

The present invention provides an intravenous fluid supply device that periodically extrudes a predetermined amount of an infusion fluid at regular time intervals in a manipulated manner, regardless of the position of an infusion bag, enables round-the-clock real-time visual checking for normal supply of an infusion fluid without using a conventional drop pipette, guarantees safety by activating an alarm when air is included in an infusion fluid or when the fluid is injected excessively or insufficiently, and offers convenience of being portable by having compactness and realizing lower-current consumption than the conventional art.

An infusion fluid has to be administered at a constant rate at regular time intervals.

First, it is known that an infusion fluid can be stably administered without blood backflow when an infusion bag is placed to be about 80 cm higher than a patient's heart because an appropriate pressure for injection of an infusion fluid can be maintained at that height. To this end, a hanger is typically used to maintain the height of an infusion bag. When an infusion fluid is injected based on the gravity, a patient or nurse has to be always careful that the height of an infusion bag is adequate. For this reason, when a patent moves, the patient has to carry a hanger with an infusion bag hung on it or a nurse has to accompany the patient, raising the infusion bag to an adequate height.

Alternatively, a pressing means for obtaining an adequate pressure can be used. For example, there is an infusion fluid injection method that injects an infusion fluid by indirectly pressing an infusion fluid storage container using expanding force of compressed air or highly pressurized gas that can press an infusion bag, or using a gas that is diffused into a piston at a predetermined speed.

Further alternatively, it is possible to press an infusion bag by pressing a pressing plate using recovery force of a coil spring or screwing of a motor.

Yet further alternatively, injection of an infusion fluid can be performed by pressing an infusion bag by slowly winding an infusion bag around a roller using recovery force of a clockwork device or rotation of a motor.

Each of these methods requires use an additional complex device for pressing the infusion bag.

Second, a peristaltic pump or a roller-type pump is generally used to electronically control an appropriate injection speed.

A peristaltic pump sequentially operates pressing fingers by driving cam arrays that are distanced from each other by a predetermined angle, thereby inducing a linear wave motion. This linear wave motion moves a liquid contained in a tube, thereby extruding the liquid.

A roller-type pump performs injection of an infusion fluid by moving a liquid contained in a tube in such a manner that a plurality of rollers rotate and internally touch the surface of a cylindrical tube to discharge the liquid. According to the injection method using pumps, an infusion fluid is supplied by a motor. Accordingly, the motor needs to be continuously activated at a controlled predetermined speed. When it is necessary to inject an infusion fluid for a long period, an activation time of the motor is long, which results in consumption of a large amount of current. Therefore, the injection method using a pump is an inefficient injection method. Furthermore, because of consumption of a large amount of current, a large battery has to be used. Therefore, an infusion fluid supply device employing this method is inevitably large and heavy, and thus is not portable.

DISCLOSURE

Technical Problem

Accordingly, the present invention has been made keeping in mind the above problems occurring in the prior art, and an object of the present invention is to provide an intravenous fluid supply device that can safely and automatically inject a constant amount of an infusion fluid at regular time intervals using a microprocessor technology.

A first object of the invention is to provide an intravenous fluid supply device that offers convenience in use by enabling an infusion fluid to be injected regardless of whether an infusion fluid storage container (infusion bag) is placed to be higher or lower than the part (human body) into which an infusion fluid is injected.

A second object of the invention is to provide an intravenous fluid supply device in which a geared motor, which is the main driving source of an extrusion means, is not continuously activated but is instantly activated at an inputted repetition cycle, thereby reducing the amount of power consumption substantially and thus enabling application of a small power storage scheme. In addition, the second object provides the economic merit of low cost by realizing a compact and low-cost product.

A third object of the invention is to provide an intravenous fluid supply device that enables round-the-clock visual checking for normal supply of an infusion fluid without using a conventional drop pipette.

The intravenous fluid supply device according to the third object guarantees safety by activating an alarm when air is included in an infusion fluid, when an infusion fluid is injected excessively or insufficiently, when a preset total amount of injection is reached, or when a battery voltage is below a preset value.

Technical Solution

Hereinafter, embodiments of the present invention will be described in detail with reference to the accompanying drawings.

FIGS. 1 and 2 are a plan view and a right side view, respectively, illustrating appearance of an intravenous fluid supply device according to one embodiment of the present invention. The intravenous fluid supply device 100 is a compact device that operates on batteries. The device 100 can be attached to an infusion bag. The device 100 can set an extrusion and injection cycle and a total amount of an infusion fluid supplied. When a start button is pressed, the device 100 can automatically supply a predetermined amount of an infusion fluid at a predetermined cycle. When the preset total amount of an infusion fluid is supplied, the device 100 automatically stops operating.

FIG. 3 is an enlarged plan view illustrating a body 1 from which a cover 2 is removed. A battery 7 is installed in a left portion of the body 1 and a control board 8 is installed in a right portion of the body 1. A microcontroller 8, which is a control means B that controls operation of an extrusion means A, and an LCD 65 are mounted on the control board 8. Reference number 34 denotes a support that supports the control board 8. The extrusion means A that supplies an infusion fluid is mounted in the center of the body.

Hereinafter, the extrusion means A will be described in detail.

FIG. 4 is a plan view of the body 1 with which an infusion fluid set 11, which is a main component of the extrusion means A, is not yet combined. FIG. 6 is the structure that is obtained after a spike 12 of the infusion fluid set 11 illustrated in FIG. 5 and a sealing cap 10 of an infusion bag 9 are combined with each other and the combined structure of the spike 12 and the sealing cap 10 is inserted into an inside space 5 of the body 1.

A cam housing 19 and periphery components of a motor 15 with which a cam 16 is engaged are installed on the top surface of the body 1 after the structure of FIG. 6 is assembled so that an L-shaped protruding portion 18 of a motor fixing plate 17 presses an elastic tube 33. The resultant structure is illustrated in FIG. 3.

FIG. 7 is a perspective view illustrating the cam housing 19 and the motor 15 with which the cam 16 is engaged. FIGS. 8(a) to 8(d) illustrates a perspective view, a left side view, a front view, and a right side view illustrating both the motor 15 with which the cam 16 is engaged, and periphery components. FIGS. 9(a) to 9(d) illustrates a perspective view, a left side view, a front view, and a right side view illustrating the cam housing 19 and periphery components.

Since the motor 15 used in the present invention needs to have a compact size and a large torque, the motor 15 may be preferably a geared motor.

First, the motor 15 and periphery components will be described below in detail.

With reference to FIGS. 8(a) to 8(d), the motor 15 with which the cam 16 is engaged is mounted on the motor fixing plate 17 and a hall sensor 67 is attached to the motor fixing plate 17. A portion of the motor fixing plate 17 is punched to form the L-shaped protruding portion 18. The motor fixing plate 17 is rotatably engaged with a shaft 23. A biaxial shaft 23 is fixed to a support plate 24.

Since an outer periphery surface of the cam 16 has a bearing structure, its frictional resistance is minimized.

Second, the cam housing 12 and the periphery components will be described below.

With reference to FIGS. 9(a) to 9(d), a cam receiving space 20 is formed in a right side surface of the cam housing 19 having a rectangular parallelepiped shape so that the cam 16 can be received in the cam receiving space 20 and can horizontally slide. As illustrated in FIGS. 7 to 8(d), in a right lower end portion in a front surface of the cam housing 19, a permanent magnet 22 is buried in a position corresponding to the hall sensor 67 in order to control the activation of the motor 15. A vertically elongated bolt 21 is buried in the cam housing to adjust a position of the elastic tube 33 pressed, thereby adjusting an amount of an infusion fluid for one injection. As illustrated in FIGS. 8(a) to 10(b), a pin 2 is fixed to a left surface of the cam housing 19, one end of a tension spring 27 is engaged with the pin 25, and the opposite end of the tension spring 27 is engaged with a pin 26 that is fixed to the body 1. The cam housing 16 and the motor fixing plate 17 are engaged with the same shaft 23. Therefore, when the cam housing 19 is lifted in the direction of an arrow of FIG. 10(b), the lifted state is maintained due to fly-back action of the tension spring 27. This allows the infusion fluid set 11 to be easily replaced.

In the state of FIG. 10(a), the tension of the tension spring 27 is stronger than the pressing force of the protruding portion 18 of the motor fixing plate 17 that presses the elastic tube 33. Therefore, the cam housing 25 is not raised during extrusion, so that the extrusion action is guaranteed.

Third, the infusion fluid set 11 will be described below.

As illustrated in FIG. 5, the infusion fluid set 11 includes the spike 12, the elastic tube 33 in which a suction check valve 40 and an extrusion check valve 50 are installed, a see-through pipe 28, an IV infusion fluid supply pipe 13, and an infusion fluid needle 14. Each of the components will be described below.

The spike 12 is an insertion needle to be combined with the sealing cap 10 of the infusion bag 9.

An end of the elastic tube 33 is elastically inserted into the spike 12 and the opposite end of the elastic tube 33 is elastically inserted into an inflow side of the see-through pipe 28. An end of the IV infusion fluid supply pipe 13 is elastically inserted into an outflow side of the transparent 28 and the opposite end of the IV infusion fluid supply pipe 13 is elastically inserted into the infusion fluid needle 14.

The structure of the suction check valve 40 will be described below.

As illustrated in FIGS. 11(a) and 11(b), the suction check valve 40 is structured as follows: an orifice 42 is bored in an end portion of an inlet 41 of the suction check valve 40; a protrusion pin 45 protrudes toward a suction check valve body 44 in which a valve seat 43 is formed; a cap 47 with an outlet 46 is inserted; a valve plate 49, which is an elastic circular rubber plate with a plurality of protrusions 48, is inserted into a space provided between the valve seat 43 and the cap 47 so as to be situated in the center of the valve seat 43; and the protrusion pin 45 protrudes such that the valve plate 49 smoothly comes into contact with the valve seat 43.

The valve plate 49 of the suction check valve 40 has the same shape as a valve plate 59 of the extrusion check valve 50.

The structure of the extrusion check valve 50 will be described below.

As illustrated in FIGS. 12(a) and 12(b), an inlet 51 is bored; a protrusion pin 55 protrudes toward an extrusion check valve body 54 in which a valve seat 53 is formed; a cap 57 with an orifice 52 is inserted into an end of an outlet 56 of the extrusion check valve 50; a valve plate 59, which is an elastic circular rubber plate with a plurality of protrusions 58, is inserted into a space provided between the valve seat 53 and the cap 57 so as to be situated in the center of the valve seat 53; and the protrusion fin 55 protrudes such that the valve plate 59 strongly comes into contact with the valve seat 53.

As illustrated in FIGS. 15(a) and 15(b), the valve plate 59 of the extrusion check plate 50 has a thickness t that is larger than that of the valve plate 49 of the suction check valve 40 or is more rigid than the valve plate 49 of the suction check valve 40. The valve plate 59 of the extrusion check valve 50 strongly comes into contact with the valve seal 53 so that backflow can be prevented.

The structure of the see-through pipe 28 will be described below.

As illustrated in FIGS. 14(a) and 14(b), the see-through pipe 28 is transparent. A first buoy 29 that is not harmful to the health of a human body and has lower specific gravity than an infusion fluid is inserted into an introduction hole of the see-through pipe 28 and a second buoy 30 that is not harmful to the health of a human body and has higher specific gravity than the infusion fluid is inserted into an exit hole of the see-through pipe 28. Therefore, it is possible to be aware of the flow of an infusion fluid from the movement of the buoys 29 and 30 regardless of the position or direction of the intravenous fluid supply device 100. At night, it is possible to check the flow of an infusion fluid using a backlight LED 66 that flashes as soon as the motor 15 is activated.

The IV infusion fluid supply pipe 13 and the infusion fluid needle 14 are conventional components.

The check valves 40 and 50 may be made of a synthetic resin that is not harmful to the health of a human body and is approved as a material that can be used for medical purposes. The elastic tube and valve plates 49 and 59 may be made of any material as long as the material has elasticity and flexibility so as to expand and contract like silicone or latex, is not harmful to the health of a human body, and is approved as a material that can be used for medical purposes.

FIGS. 16, 17, and 18 are right side views of the extrusion means A that is mounted in the body 1 after the infusion bag 9 and the extrusion means A are combined with each other. The cover 2 is opened or closed by means of a hinge 3 and can be securely locked using a latch 4.

The see-through pipe 28 is installed to be near the cover 2 and has an inspection hole 31 provided with an inspection window 32 through which the movement of the buoys 29 and 30 can be checked. Although not illustrated in the drawings, the LCD 65 may have an inspection hole and an inspection window in the corresponding positions.

Next, the control means B will be described below.

The control means B includes: an input means 200 that enables setting of a repetition cycle of the motor 15 and a total amount of injection and enables inputting of a start or stop command; a detection means 300 that includes a sound sensor that detects whether air intrudes into an infusion fluid or a hall sensor 67 that detects a top dead center (TDC) of the motor fixing plate 17; a motor driving means 400 that drives the motor 15 to extrude an infusion fluid; a microcontroller 500 that controls the motor driving means 400 according to an input sent from the detection means 300 and the input means 200; a display means LCD 600 that displays remaining battery power, a preset total amount of injection, and an extrusion repetition cycle in which a user checks equipment for normal operation according to the control of the microcontroller 500; an LED lighting means 700 that is a backlight of the see-through pipe 28 that allows a user to check for normal flow of the infusion fluid even at night according to the control of the microcontroller; an alarm means 800 that activates an alarm according to the control of the microcontroller 500 when a battery voltage is low, an amount of an infusion fluid that is injected is excessive or insufficient, air is included in the infusion fluid, or when a total amount of injection is reached; and a direct current power supply means 900 that supplies driving power to the microcontroller 500 or the individual components.

Power switch 60: a switch to turn on or off a power supply of the intravenous fluid supply device 100.

Charging button 61: a button for water charging (air purging). When the button is pressed after the infusion bag 9 is connected, the infusion fluid set 11 is filled with the infusion fluid. While it is being pressed, the motor 15 is continuously activated regardless of the detection result of the detection means 300.

Start/Stop switch 62: a switch to start or stop operation of the device. The microcontroller 500 performs energy saving mode to reduce power consumption according to the position of this switch.

Motor 15: a geared motor that serves as a driving source to press the elastic tube 33.

LCD 65: a display device for visual recognition. This device displays the total number of times of extrusion, a total amount of injection, and remaining battery power. This device also displays an error message if a fault occurs.

Hall sensor 67: a micro switch may be used as a means for detecting the position of a top dead point of the motor fixing plate 17. According to the present invention, the hall sensor 67 is used as the means for detecting.

Sound sensor 68: a kind of mike or sensor that detects noisy sound that is made at the time of suction or extrusion of the infusion fluid if air is included in the infusion fluid, and that converts the detected sound into an electrical signal.

The sound sensor 68 is installed in each of the main part 6 shown in FIG. 4 so as to be in close contact with the suction check valve 40 or the extrusion check valve. It functions to detect air bubbles in the infusion fluid at the time of suction or extrusion of the infusion fluid.

Alarm means 800: an alarm device for audio recognition. This device notifies starting, stopping, and abnormal conditions. A buzzer driving unit is included to activate a buzzer by amplifying a signal of the microcontroller 500. The alarm means raises an alarm when air is included in an infusion fluid, a battery replacement time becomes closer, a preset total amount of injection is reached, or when an infusion fluid is supplied excessively or insufficiently.

Extrusion repetition cycle setting dial 63: a variable resistance control for setting an extrusion repetition cycle. The extrusion repetition cycle setting dial is operated such that the microcontroller 500 reads the value of the variable resistance and activates an internal timer.

Total injection amount setting dial 64: a variable resistance for setting a total injection amount. The total injection amount setting dial is operated such that the microcontroller 500 reads the value of the variable resistance, and multiplies an amount of an infusion fluid for a single injection by the number of times of extrusion to obtain a total amount of injection. When the total amount of injection reaches a preset injection amount, the alarm is produced and the operation of the device is stopped.

LED 66: a backlight light-emitting diode that illuminates the see-through pipe 28 to enable visual inspection on the flow of an infusion fluid at nighttime Advantageous Effects The intravenous fluid supply device according to the present invention safely and automatically injects a predetermined amount of an infusion fluid at regular time intervals using a microprocessor technology.

The intravenous fluid supply device according to the present invention offers convenience in use by enabling an injection of an infusion fluid regardless of the position of an infusion fluid storage container (infusion bag), i.e., whether the infusion bag is placed to be higher or lower than the part (human body) to which the infusion fluid is injected.

A geared motor, which is the main driving source of the extrusion means, is not continuously activated but is instantly activated at an inputted repetition cycle, thereby reducing the amount of power consumption substantially and enabling application of a small power storage scheme. In addition, an extrusion means, a control means, and a battery are integrally received in a body, thereby minimizing the number of components and simplifying the structure. This enables compactness of a product, improves portability of a product, and provides the economic merit of low cost.

The intravenous fluid supply device according to the present invention enables round-the-clock visual checking for normal supply of an infusion fluid without using a conventional drop pipette and enables normal supply of an infusion fluid regardless of its position, i.e., regardless of whether the intravenous fluid supply device is placed vertically or horizontally or whether the intravenous fluid supply device is placed to be higher or lower than an injection spot. The intravenous fluid supply device according to the invention guarantees safety by activating an alarm when air is included in an infusion fluid, when an infusion fluid is injected excessively or insufficiently, when a preset total amount of injection is reached, or when a battery voltage is below a preset value.

DESCRIPTION OF DRAWINGS

FIG. 8(*b*) is a left side view of the structure of FIG. 8(*a*);

FIG. 8(*c*) is a front view of the structure of FIG. 8(*a*);

FIG. 8(*d*) is a right side view of the structure of FIG. 8(*a*);

FIG. 9(*b*) is a left side view of the structure of FIG. 9(*a*);

FIG. 9(*c*) is a front view of the structure of FIG. 9(*a*);

FIG. 9(*d*) is a right side view of the structure of FIG. 9(*a*);

FIGS. 10(*a*) and 10(*b*) are cross-sectional views of the body of the present invention, in which:

FIG. 10(*a*) illustrates a normal state in which the cam housing of the extrusion means and a geared motor of are safely mounted; and FIG. 10(*b*) illustrates a rotated state in which an end of the cam housing of the extrusion means is lifted, and the cam housing and the geared motor that are fixed to the same shaft are collectively rotated and reversed;

FIGS. 11(*a*) and 11(*b*) are enlarged cross-sectional views illustrating a suction check valve of the present invention, in which:

FIG. 11(*a*) illustrates a normal state; and

FIG. 11(*b*) illustrates an operating state;

FIGS. 12(*a*) and 12(*b*) are enlarged cross-sectional views illustrating an extrusion check valve of the present invention, in which:

FIG. 12(*a*) illustrates a normal state; and

FIG. 12(*b*) illustrates an operating state;

FIGS. 13(*a*) and 13(*b*) are cross-sectional views illustrating an operation state of a protruding portion of a motor fixing plate and an elastic tube, in which:

FIG. 13(*a*) is a state in which an infusion fluid is suctioned as soon as the protruding portion is raised; and FIG. 13(*b*) is an operating state in which the protruding portion presses the elastic tube to extrude an infusion fluid;

FIGS. 14(*a*) and 14(*b*) illustrate a state of a see-through hole according to the position of a see-through pipe according to the present invention, in which:

FIG. 14(*a*) is an operating state of the see-through hole when an infusion fluid is injected when the see-through hole is positioned in a usual position; and FIG. 14(*b*) is an operating state of the see-through hole when an infusion fluid is injected when the position of the see-through hole is switched by 180 degrees from the usual position;

FIGS. 15(*a*) and 15(*b*) are views illustrating a valve plate of the extrusion check valve according to the present invention, in which:

FIG. 15(*a*) is a plan view; and

FIG. 15(*b*) is a right side view;

MODE FOR INVENTION

Appearance of the present invention will be described below.

Figure 1:
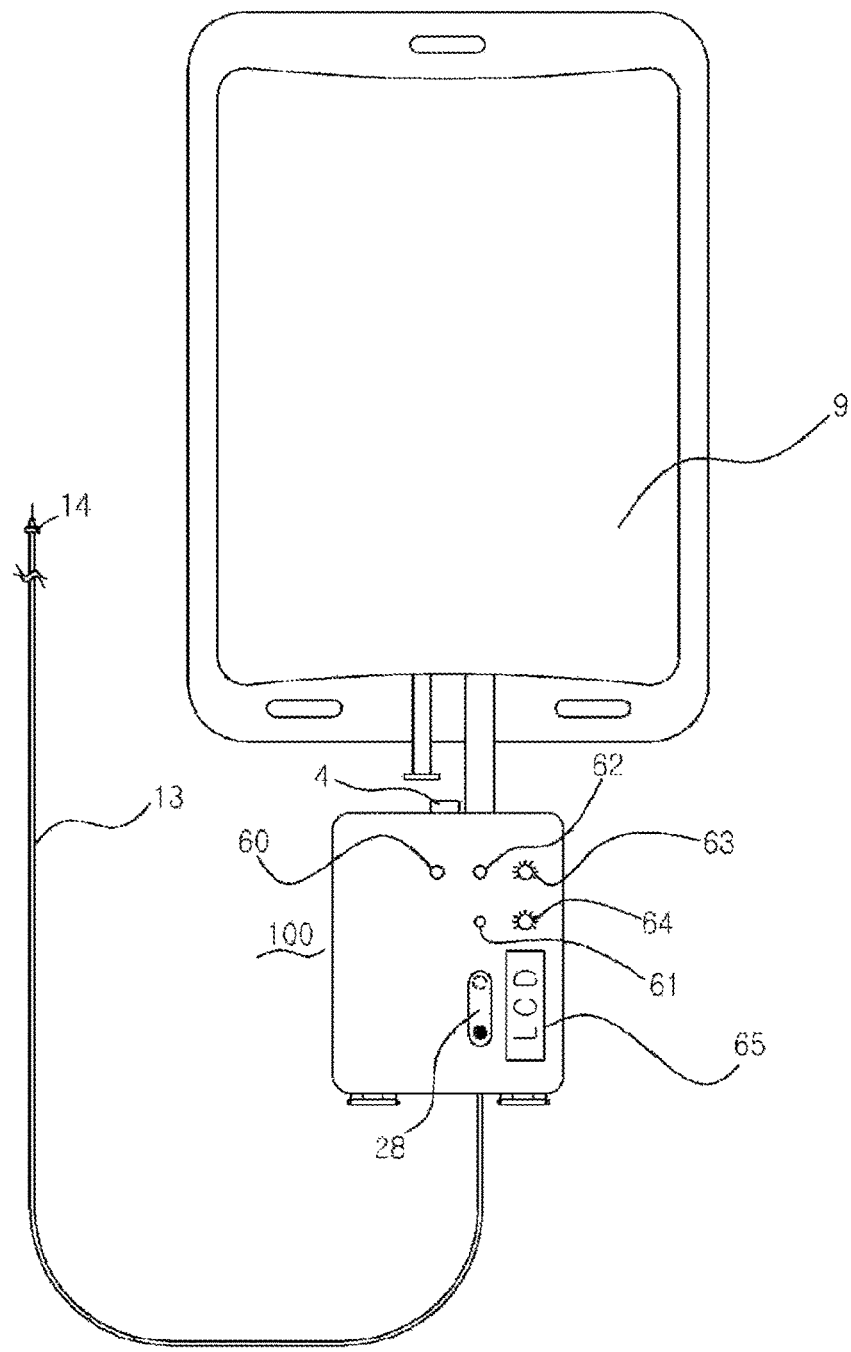
FIG. 1 is a plan view illustrating appearance of an intravenous fluid supply device according to the present invention.
Figure 2:
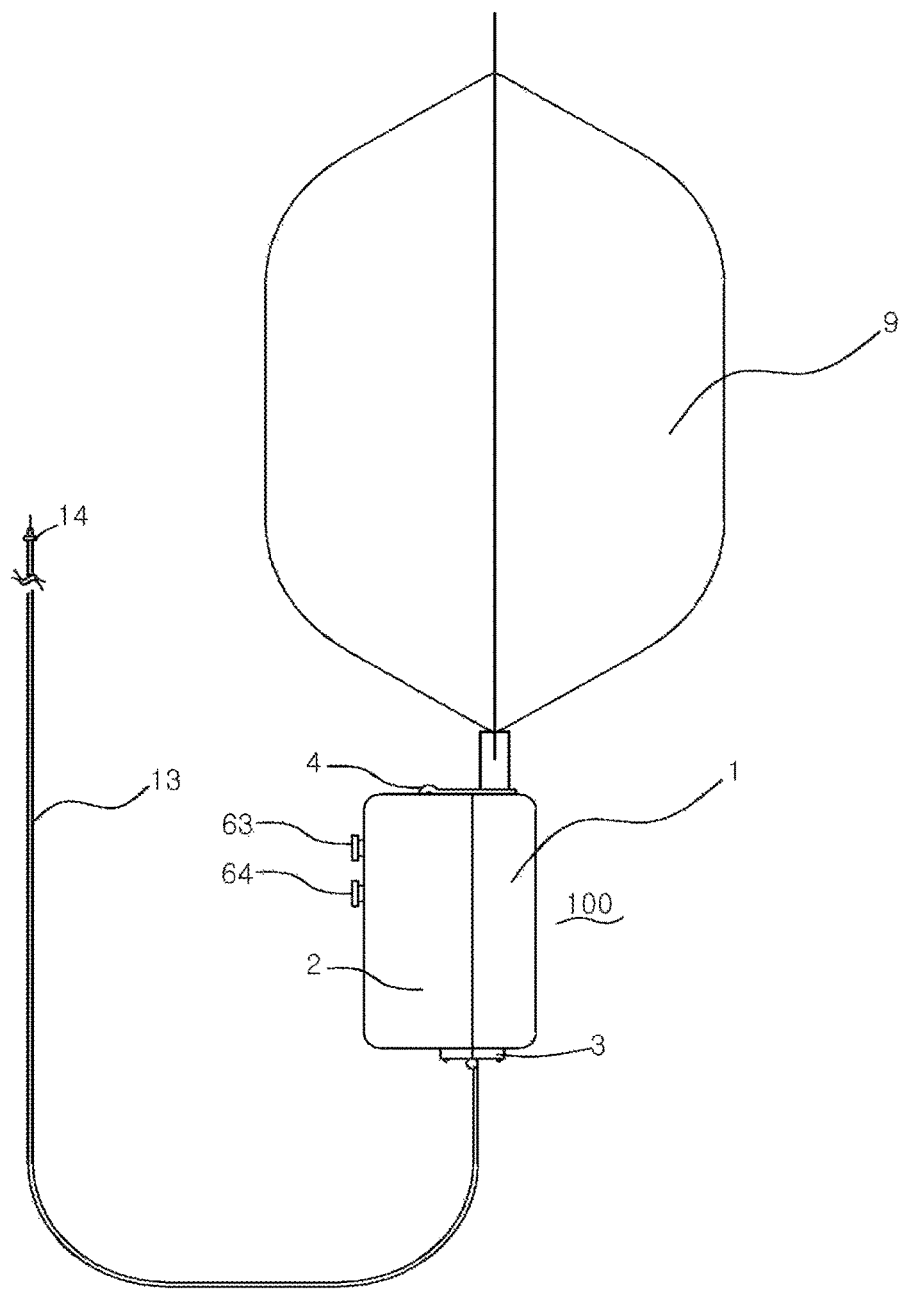
FIG. 2 is a right side view of the intravenous supply device of FIG. 1.
Figure 3:
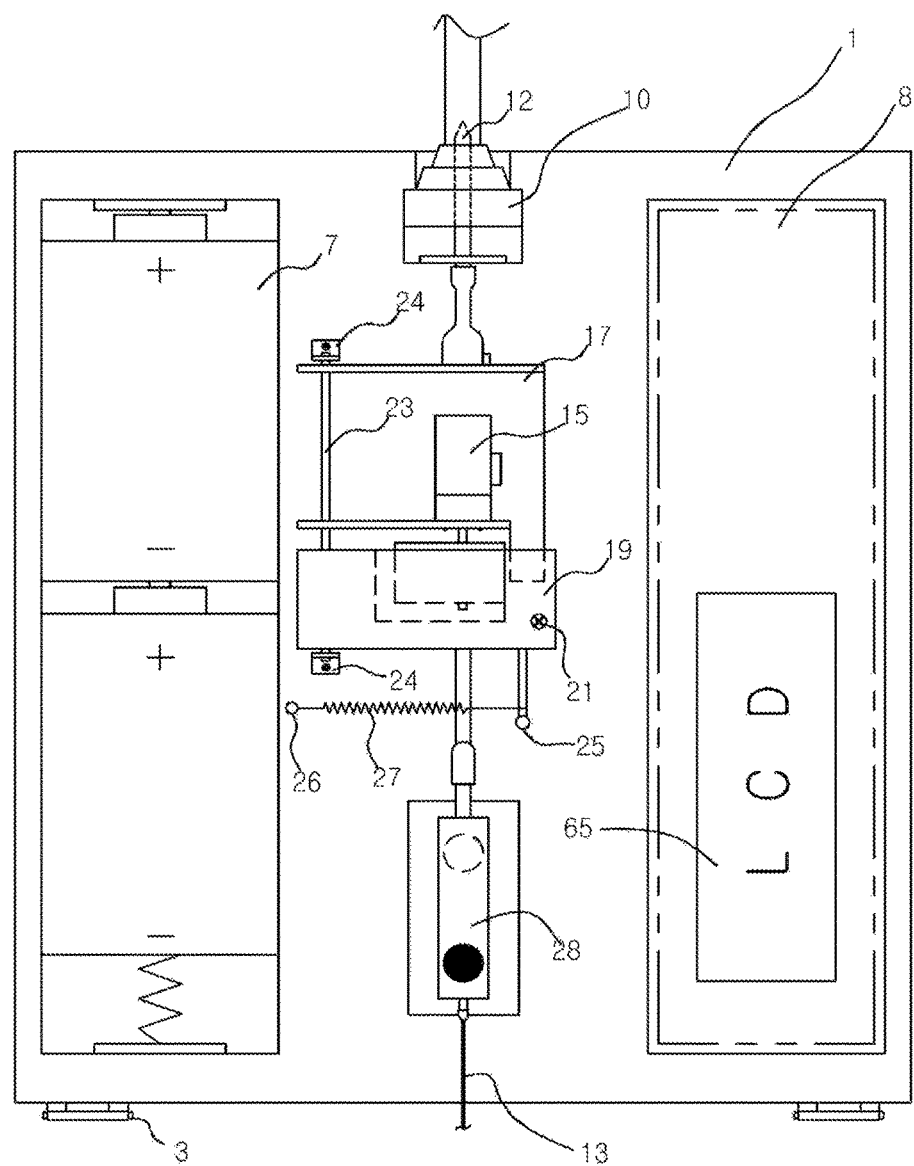
FIG. 3 is a plan view illustrating a body of the intravenous fluid supply device from which a cover is removed.

FIGS. 1 and 2 illustrate a state in which an infusion bag 9 and a body 1 are combined with each other. A repetition cycle setting dial 63 and a total injection amount setting dial 64 are attached, and values that are set using the dials 63 and 64 can be read on an LCD 65. The flow of an infusion fluid can be checked in real time through a see-through pipe 28.

A power switch 60 turns on or off a power supply of the device. A start/stop switch 62 is used to activate or deactivate the device. A charging button 61 is a button to initially charge an infusion fluid into an infusion fluid set 11. While the charging button 61 is being pressed, rapid charging is possible through continuous extrusion, regardless of the detection result of a detection means.

A cover of a body 1 can be opened or closed by means of a hinge 3 and securely locked by a latch 4. The charging button 61, the repetition cycle setting dial 63, and the total injection amount setting dial 64 are not exposed to an outside for safety purposes but are installed under the cover 2.

Installation, replacement, and function of the infusion fluid set 11 will be described below.

Figure 10:
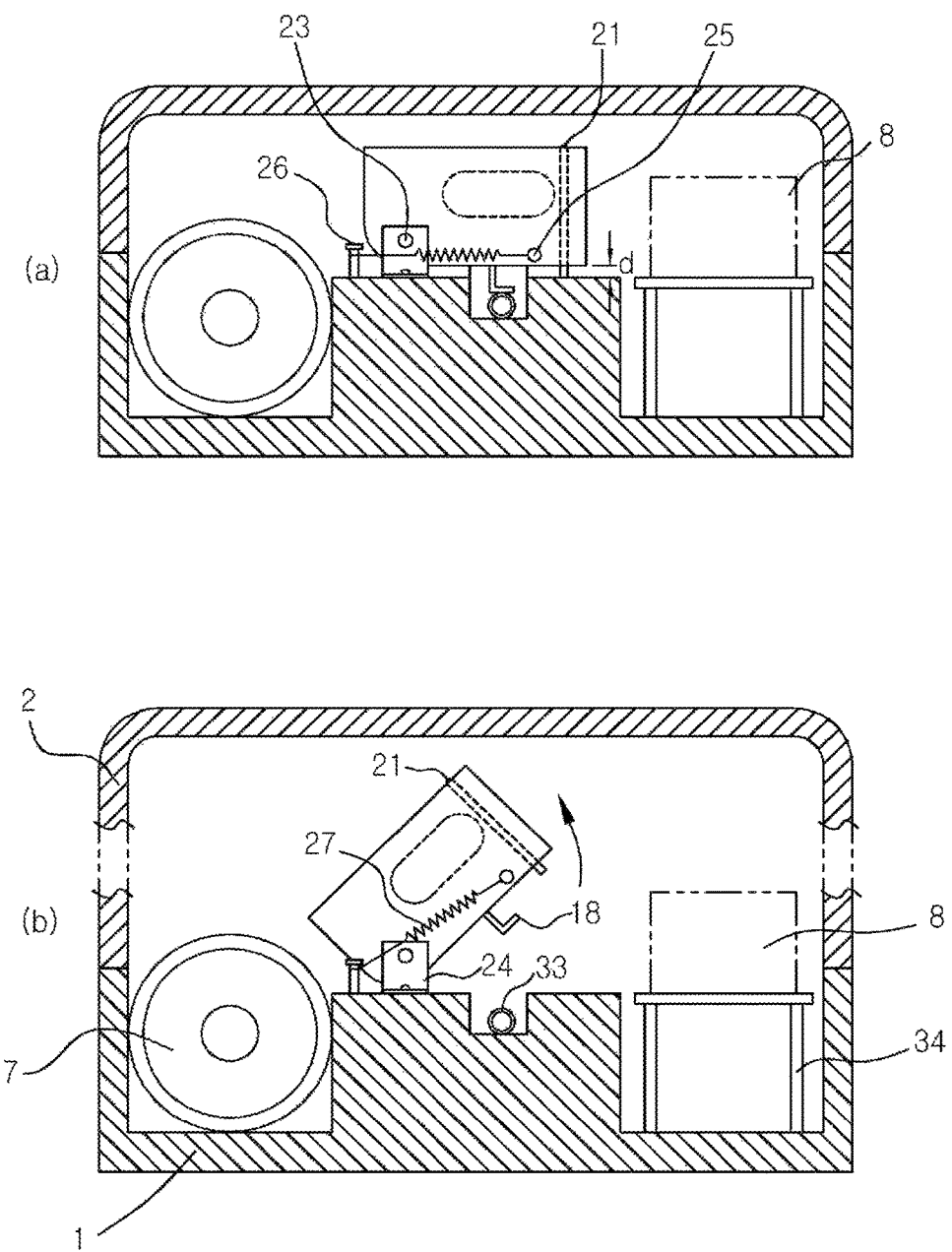
Figure 11:
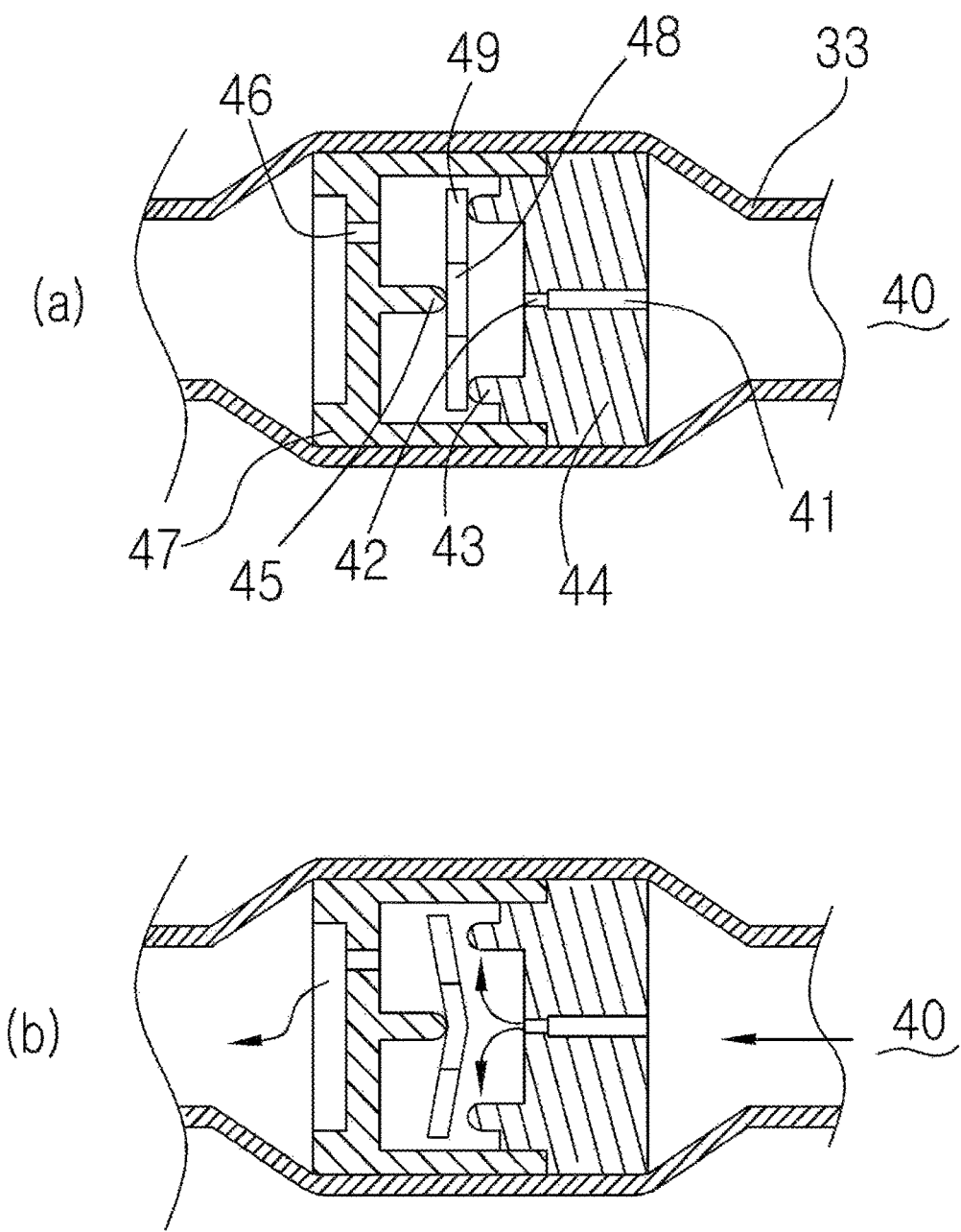
Figure 12:
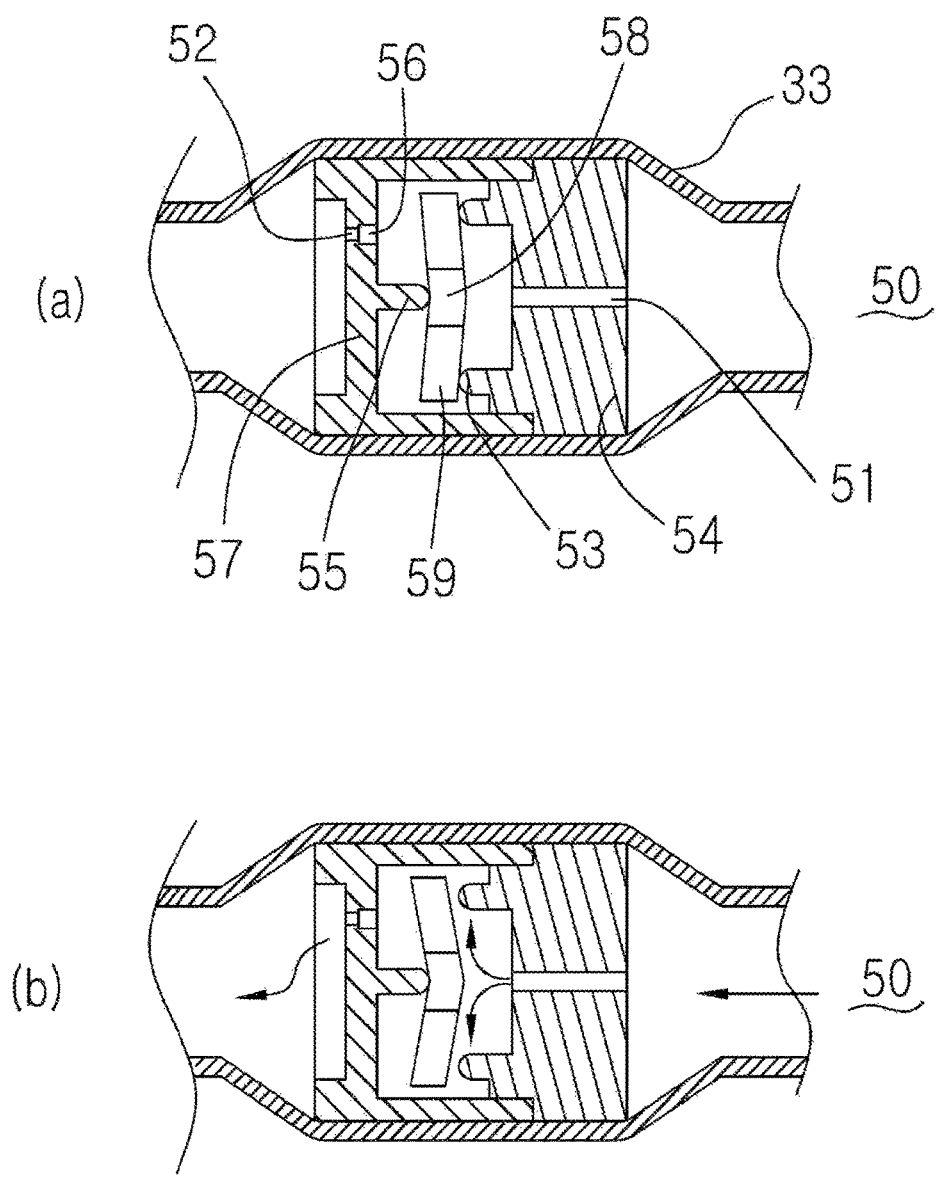

An end of a tension spring 27 illustrated in FIGS. 10(a) and 10(b) is engaged with a pin 26 that is fixed to the body 1, and the opposite end of the tension spring 27 is connected to a pin 25 that is fixed to the cam housing 27. A cam housing 19 is pivoted on or turned about a shaft 23. When installing a new infusion fluid set 11 or replacing an infusion fluid set 11, the cam housing 19 is lifted to be the state of FIG. 10(b) so that installation or replacement of the infusion fluid set 11 can be facilitated. Since the motor fixing plate 17 and the cam housing 19 are connected via the cam 16, when the cam housing 19 is lifted, the motor fixing plate 17 is also lifted along with the same shaft 23. That is, the cam housing 19 and the motor fixing plate 17 are pivoted and turned at the same time.

Figure 4:
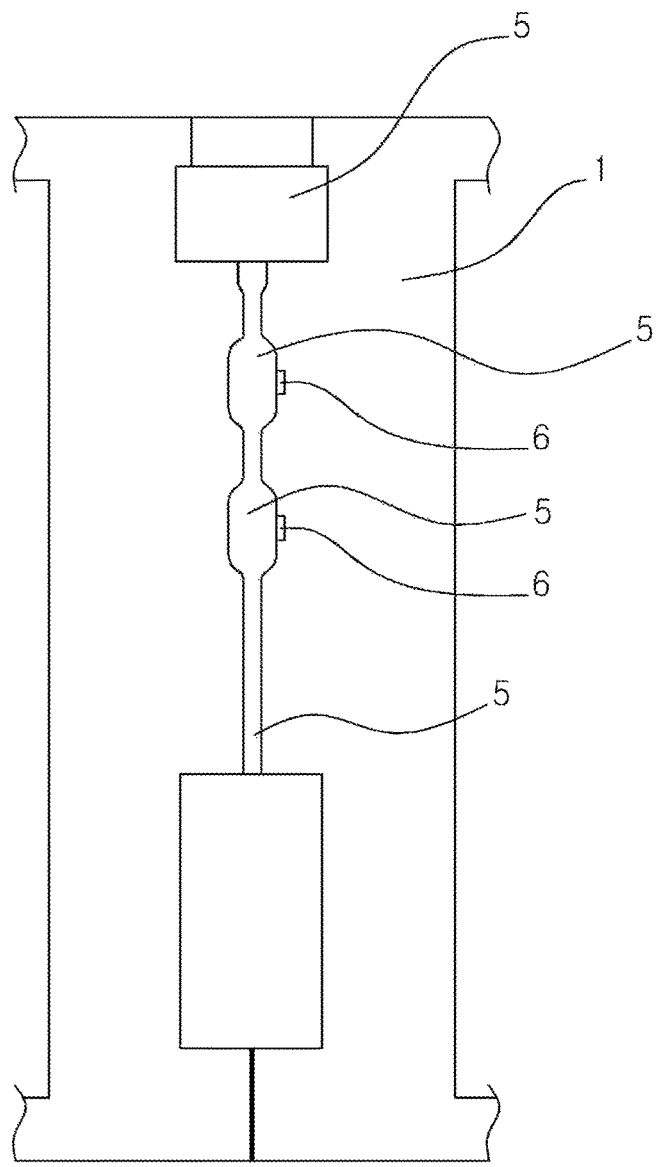
FIG. 4 is a plan view illustrating a body of the intravenous fluid supply device before an infusion fluid set of an extrusion means is combined.
Figure 5:
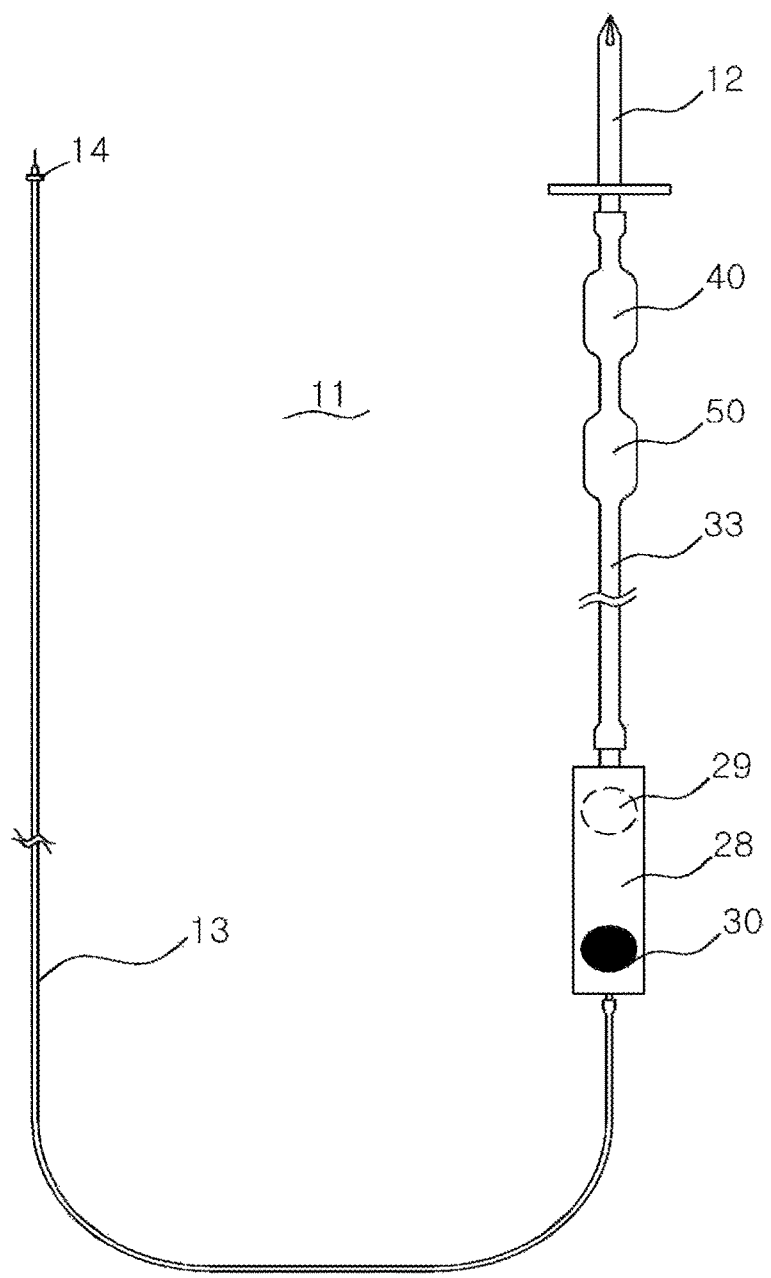
FIG. 5 is a perspective view illustrating appearance of the infusion fluid set according to one embodiment of the present invention.
Figure 6:
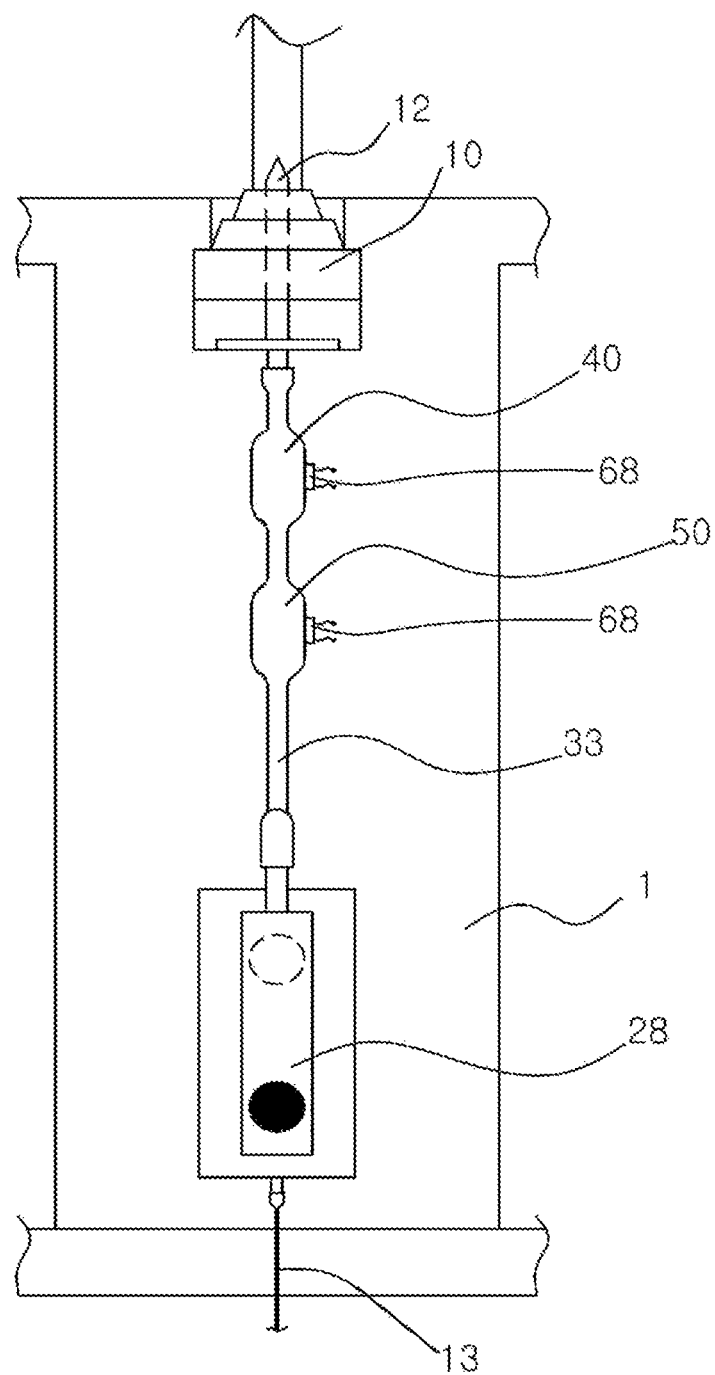
FIG. 6 is a plan view illustrating a structure that is obtained by combining a spike of the infusion fluid set of FIG. 5 and a sealing cap of an infusion bag, inserting the resultant structure into the structure of FIG. 4, and finally inserting a sound sensor.
Figure 17:
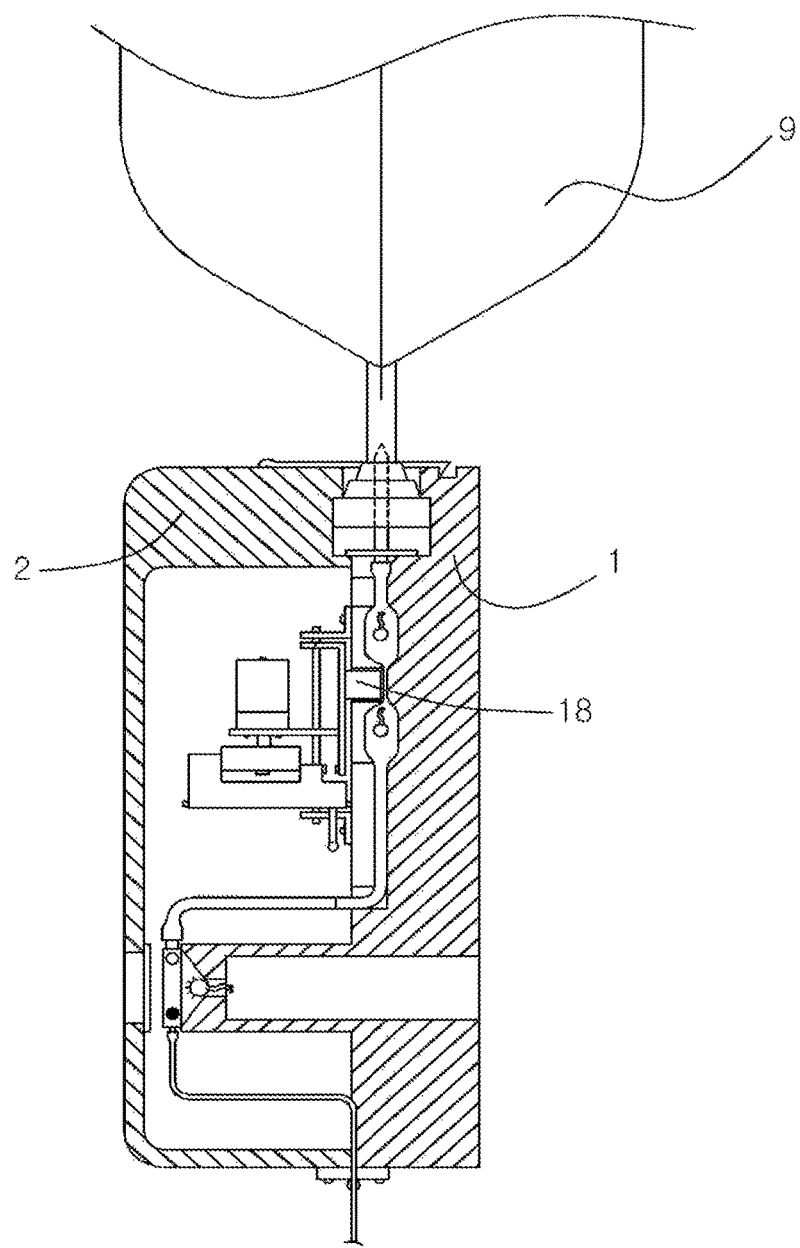
FIG. 17 is a right side view illustrating the extrusion means in a state in which an infusion fluid is extruded.
Figure 18:
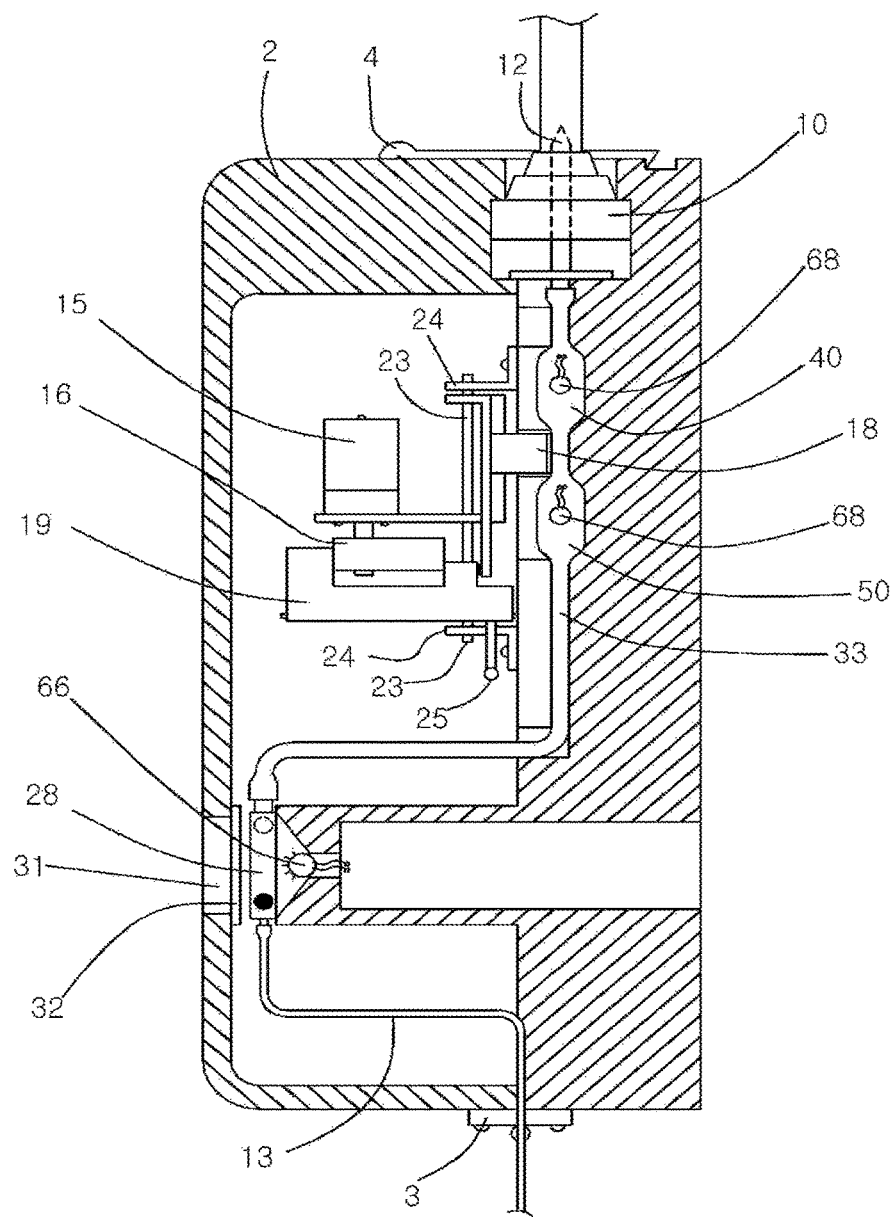
FIG. 18 is an enlarged view illustrating the structure of FIG. 16.

FIG. 6 illustrates the state in which the infusion bag 9 and the infusion fluid set 11 are combined and the resultant structure is placed in the space 5. Two sound sensors 68 are individually inserted into the main part 6 of the body 1 illustrated in FIG. 4, and then the cam housing 19 is lowered to be the structure of FIG. 10(a). Next, the cover 2 of the body 1 is closed and securely locked by the latch 4. The locked state is illustrated in FIGS. 16, 17, and 18.

The extrusion process of an infusion fluid will be described below.

Figure 13:
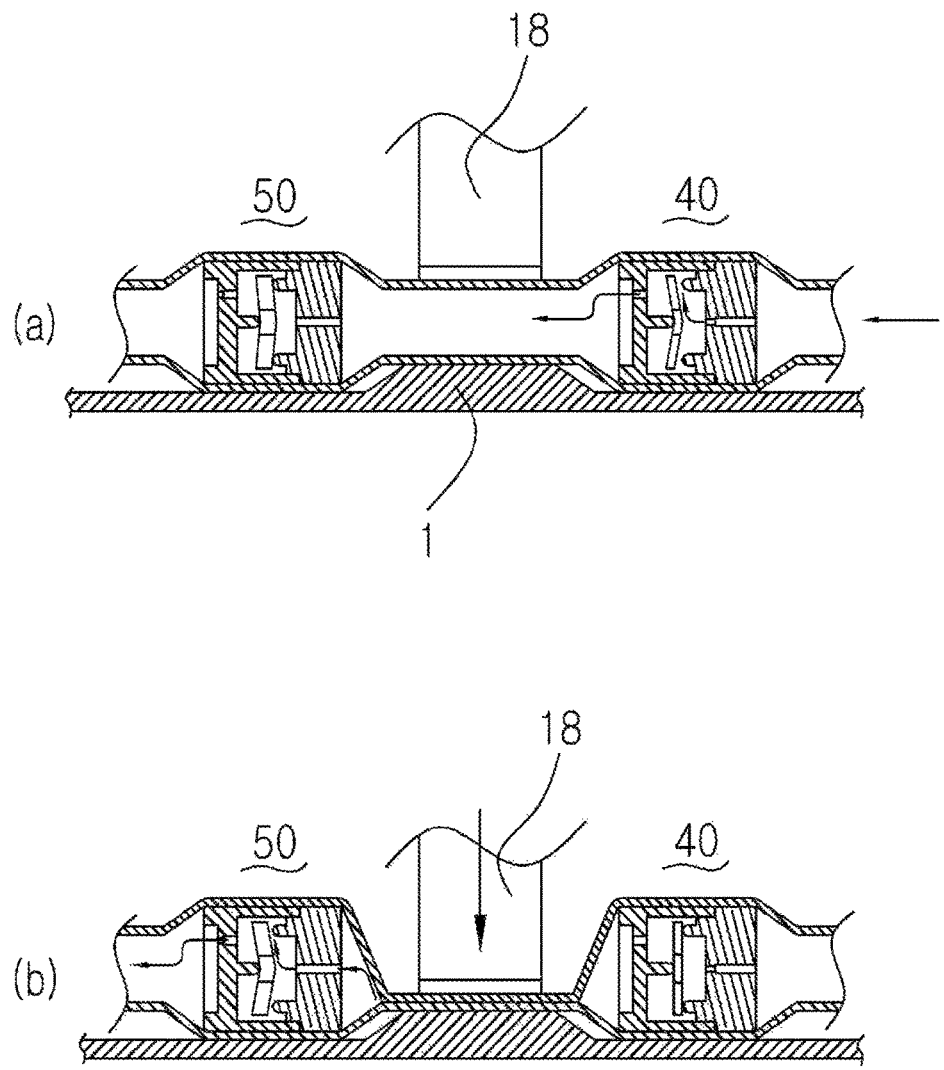
Figure 16:
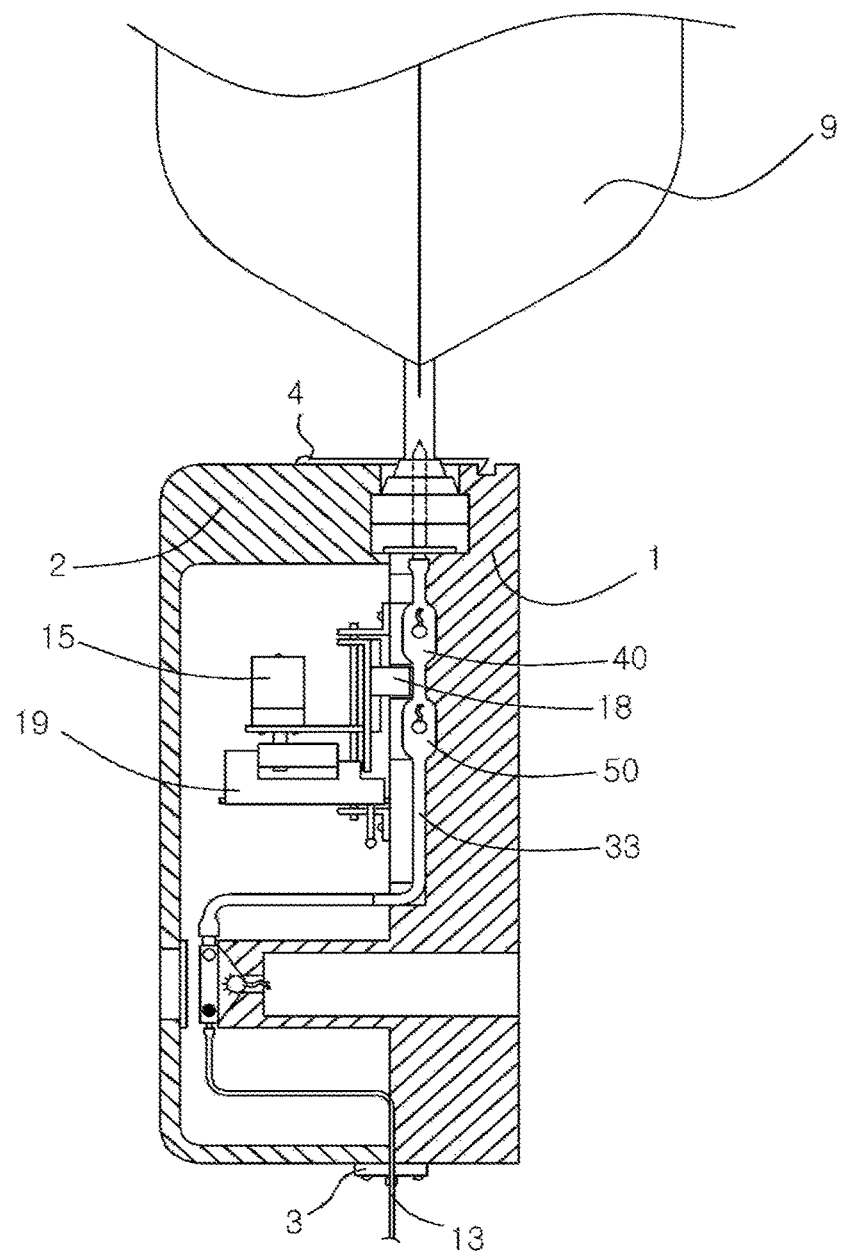
FIG. 16 is a right side view illustrating the extrusion means according to the present invention in a normal state.

FIG. 16 is a normal state in which the intravenous fluid supply device is usually positioned. The motor 15 is rotated from the state of FIG. 16, the cam 16 received in the cam receiving space 20 cannot move in a vertical direction, and the motor 15 and the motor fixing plate 17 pivot on the shaft 23 in the vertical direction. When the motor 15 is rotated, the state of FIG. 17 is formed. That is, the protruding portion 18 of the motor fixing plate 17 presses the elastic tube 33 so that the infusion fluid set is discharged. As illustrated in FIG. 13(b) in an enlarged manner, the infusion fluid pushes the valve plate 59 of the extrusion check valve 50 to be discharged.

When the motor 15 is rotated until the motor fixing plate 17 rises and reaches the top dead center, the hall sensor 67 attached to the motor fixing plate 17 approaches the permanent magnet 22 buried in the cam housing 19, detects the top dead center in contactless manner, and sends a detection signal to the microcontroller 500. Then, the rotation of the motor 15 is stopped by the control of the microcontroller 500. In this way, one cycle is completed. After that, the motor 15 is automatically rotated at the preset extrusion repetition cycle.

That is, when a cycle of up-down movement of the motor fixing plate 17 is completed, one injection of the infusion fluid is performed.

The function of adjusting an amount of extrusion will be described below.

The stroke of the motor fixing plate 17 that vertically moves up and down according to the eccentricity of the cam 16 is not variable, but a pressing area of the elastic tube 33 that is pressed can be adjusted by changing the position of the cam housing 19. This is an important element to determine an amount of extrusion for one injection. The motor fixing plate 17 and the cam housing 19 are combined via the cam 16, and the motor fixing plate 17 and the cam housing 19 are attached to the same shaft 23. Therefore, the position of the top dead center and the bottom dead center of the motor fixing plate 17 with respect to the body 1 is determined according to the relative position between the cam housing 19 and the body 1.

Figure 7:
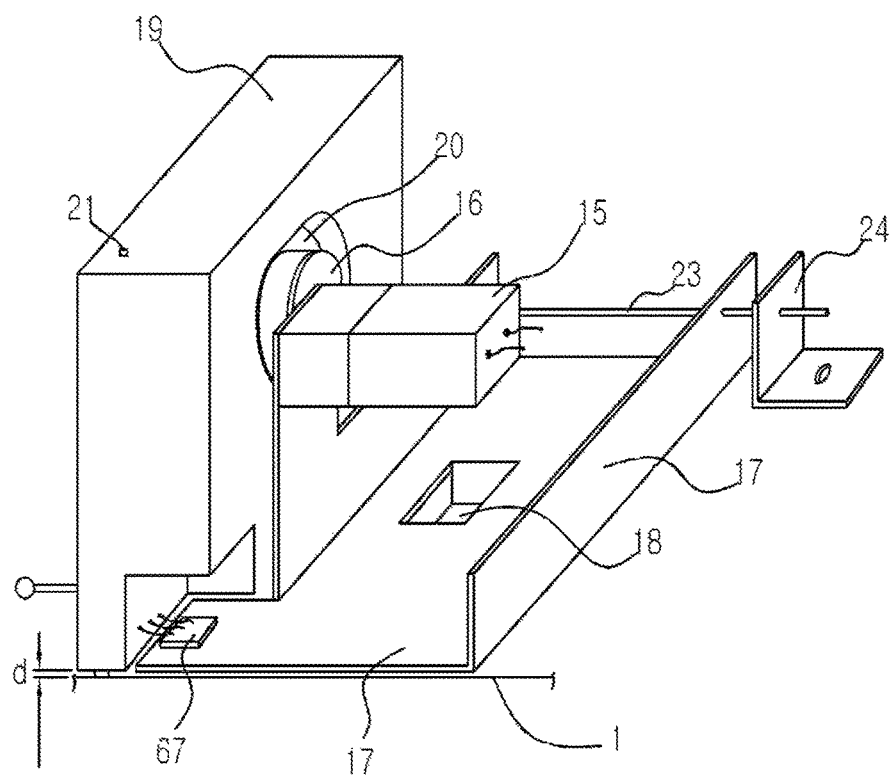
FIG. 7 is a perspective view illustrating a structure in which a motor, which is a main part of an extrusion means, and a cam housing are combined with each other.
Figure 8:
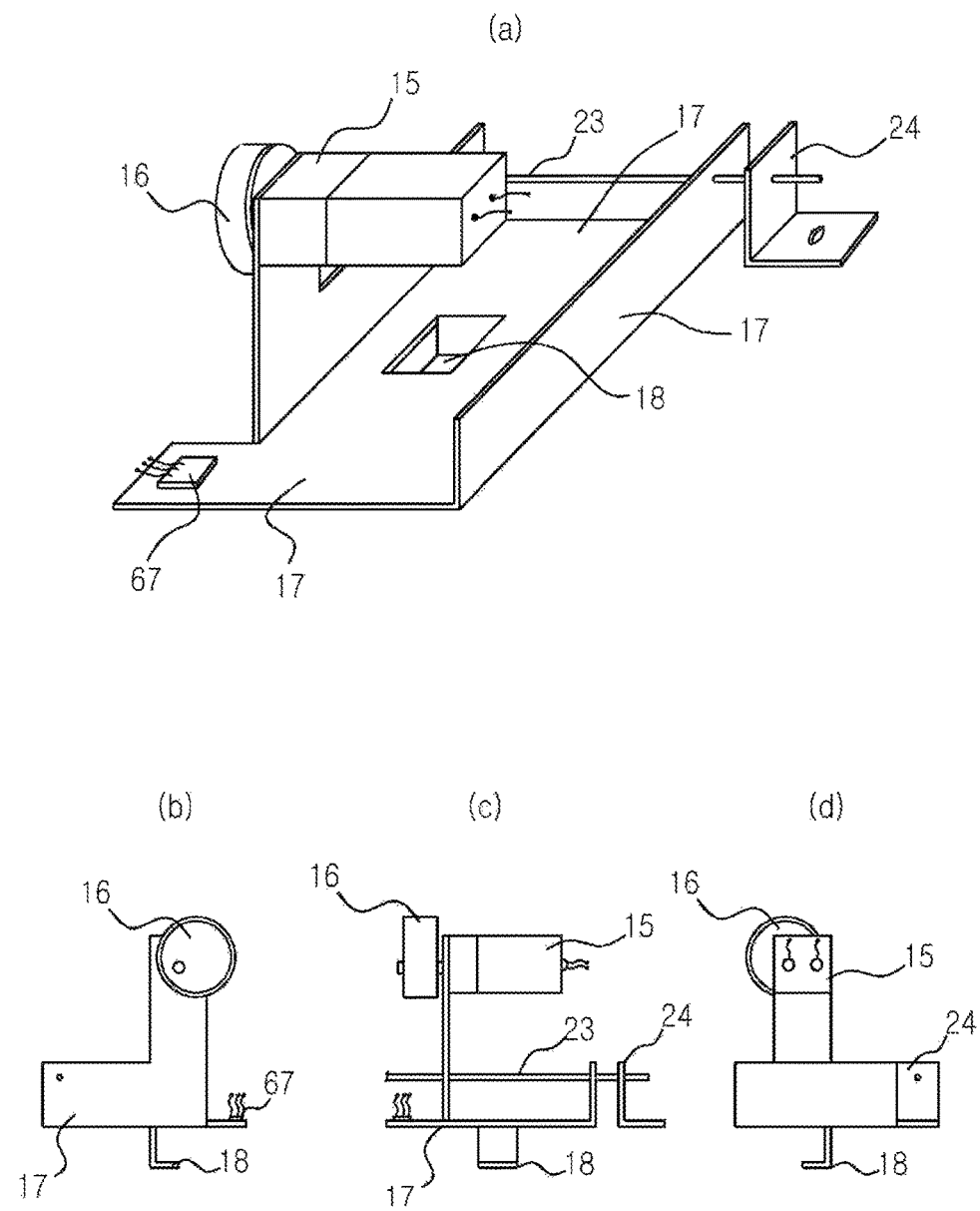
FIG. 8(*a*) is a perspective view of the motor that is a portion of the extrusion means of the present invention.
Figure 9:
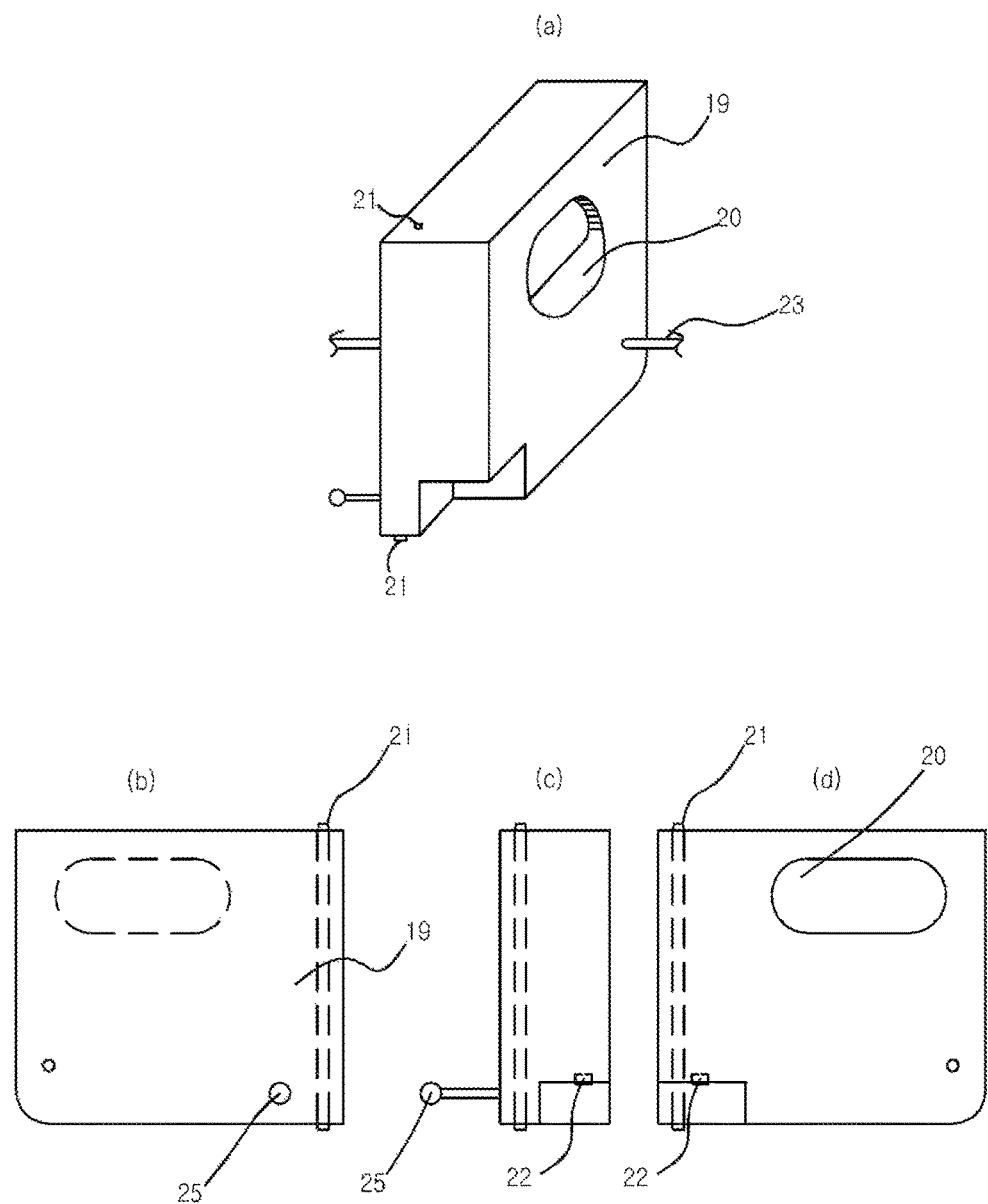
FIG. 9(*a*) is a perspective view of the cam housing, which is a portion of the extrusion means of the present invention.

As illustrated in FIGS. 7 and 10(a), a bolt 21 is vertically screwed into a front part of the cam housing 19 such that the bolt 21 protrudes toward the top surface of the body 1. This bolt 21 adjusts the gap D between the lower end of the cam housing 19 and the top surface of the body 1. This adjustment adjusts the area of the elastic tube 33 that is pressed by the protruding portion 18 of the motor fixing plate 17. In this way, the amount of extrusion for one injection is determined.

As described above, the amount of extrusion for one injection is constant. Thereby, it is possible to calculate the total amount of injection by multiplying the number of extrusions by the amount of extrusion for one injection.

The function of checking the flow of an infusion fluid according to the present invention will be described below.

The transparent see-through pipe 28 is connected to a discharge side of the infusion fluid so that the flow of the infusion fluid can be checked without using a conventional drop pipette. The first buoy 29 that is lighter than the specific gravity of the infusion fluid and the second buoy 30 that is heavier than the specific gravity of the infusion fluid are inserted in this order in the see-through pipe 28. Therefore, the flow of the infusion fluid can be monitored in real time, regardless of the direction or position of the intravenous fluid supply device 100.

The operation state of the buoys 29 and 30 will be described in detail with reference to FIGS. 14(a) and 14(b).

Figure 14:
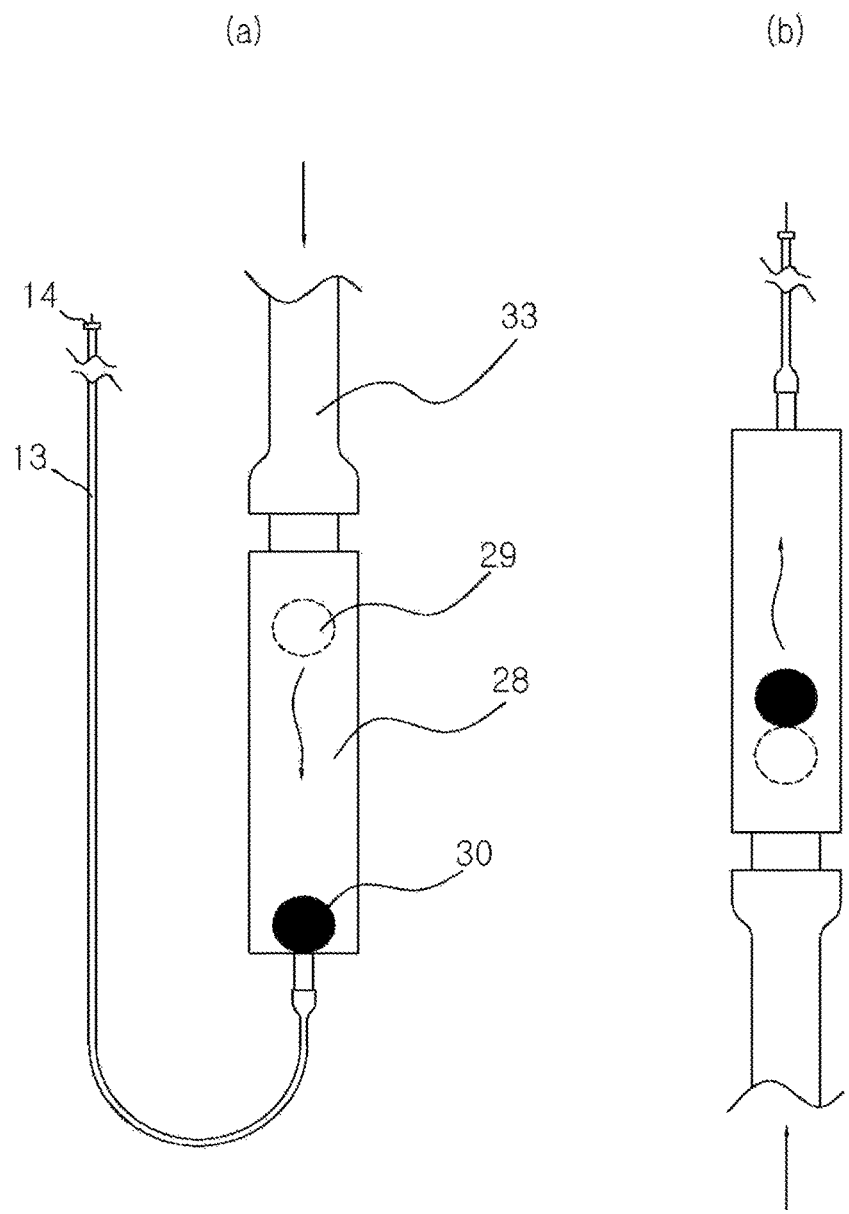
Figure 15:
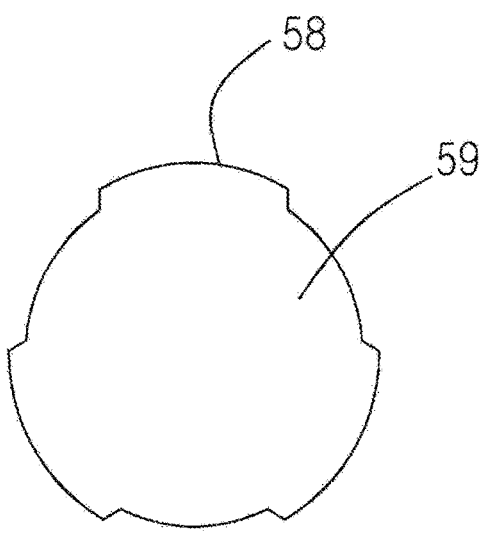
Figure 15:
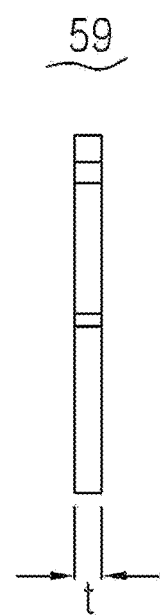

When the state of FIG. 14(a) is assumed to be a normal position, the second buoy 30 sinks and the first buoy 29 floats. When the infusion fluid is discharged, the first buoy 29 moves down so that the discharge of the infusion fluid can be checked.

FIG. 14(b) is the state that is reversed by 180 degrees from the normal position. At this point, the second buoy 30 attracts the first buoy 29 and sinks to the bottom of the see-through pipe 28. When the infusion fluid is discharged, the first buoy 29 and the second buoy 30 move up at the same time so that the movement of the buoys can be visually verified. As soon as the infusion fluid is discharged, the backlight LED 66 of the see-through pipe 28 flashes while the motor 15 is being activated. Therefore, the flow of the infusion fluid can be checked in real time even at night.

The function of the extrusion check valve 50 will be described below.

The extrusion check valve 50 is a kind of a check valve. Since the protrusion pin 55 sufficiently protrudes such that the valve plate 59 strongly comes into contact with the valve seal 53, backflow is prevented. Furthermore, the valve plate 59 is pushed by the pressure of the infusion fluid so that the infusion fluid can be extruded.

As illustrated in FIGS. 13(b) and 17, the protruding portion 18 of the motor fixing plate 17 presses the elastic hose 33 to strongly discharge the infusion fluid.

The suction check valve 40 will be described below.

The suction check valve 40 is a kind of a check valve. When the motor fixing plate 17 moves down and then up to the top dead center, the hall sensor 67 attached to the motor fixing plate 17 approaches the permanent magnet 22 buried in the cam housing 19, thereby detecting the top dead center in contactless manner and sending a detection signal to the microcontroller 500. The operation of the motor 15 is stopped according to the control of the microcontroller 500.

As soon as the motor fixing plate 17 moves up, the elastic tube recovers to its initial position due to the recovery force thereof and the infusion fluid is naturally suctioned into the elastic tube 33. When using the intravenous fluid supply device, an infusion bag is usually hung on a hanger. Since the intravenous fluid supply device is positioned in a lower end portion of the infusion bag 9, the recovery force is increased according to the position of the infusion bag 9. Whether the intravenous fluid supply device is positioned at the same position of the infusion bag 9 or is positioned higher than the infusion bag 9, the infusion fluid rises due to the recovery force of the elastic tube 33 so as to be suctioned.

The function of the hall sensor 67 according to the present invention will be described below.

The hall sensor 67 attached to the motor fixing plate 17 moves up and down by a predetermined stroke, according to the activation of the motor 15. The permanent magnet 22 that is positioned above the hall sensor 67 in the corresponding position is buried in the cam housing 19. When the motor fixing plate 17 moves down and then moves up, this state is detected in a contactless manner and the detection result is input to the microcontroller 500. This is the function of detecting the completion of one cycle.

The function of the sound sensor 68 will be described below.

The suction check valve 40 and the extrusion check valve 50 are provided with respective orifices 42 and 52. Therefore, the sound that is made when a pure infusion fluid flows and the sound that is made when an air-mixed infusion fluid flows are clearly different. The sound is detected by a detection means such as a microphone and the detection signal is processed. In this way, it is possible to check whether air is included in an infusion fluid.

The sound that is made when the air-mixed infusion fluid flows is converted into an electrical signal by a microphone. The pitch and frequency of the converted sound signal are analyzed to differentiate signals within a specific band. In this way, it is possible to check whether air is included in an infusion fluid.

The signal processing is performed through amplification, filtration, and frequency analysis.

Figure 19:
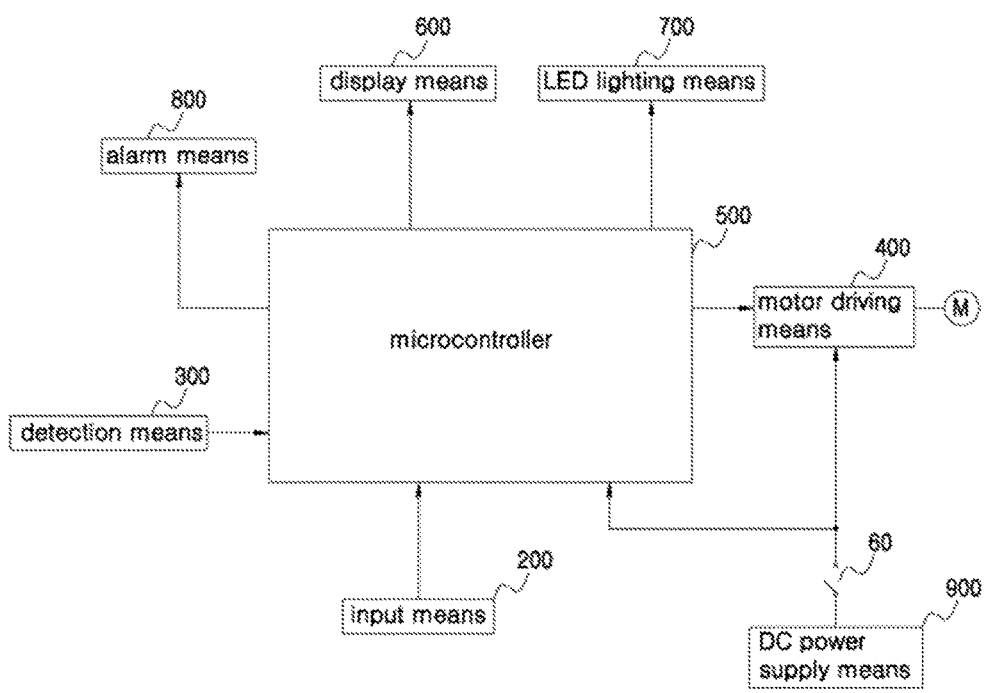
FIG. 19 is a control block diagram of a microcontroller according to the present invention.
Figure 20:
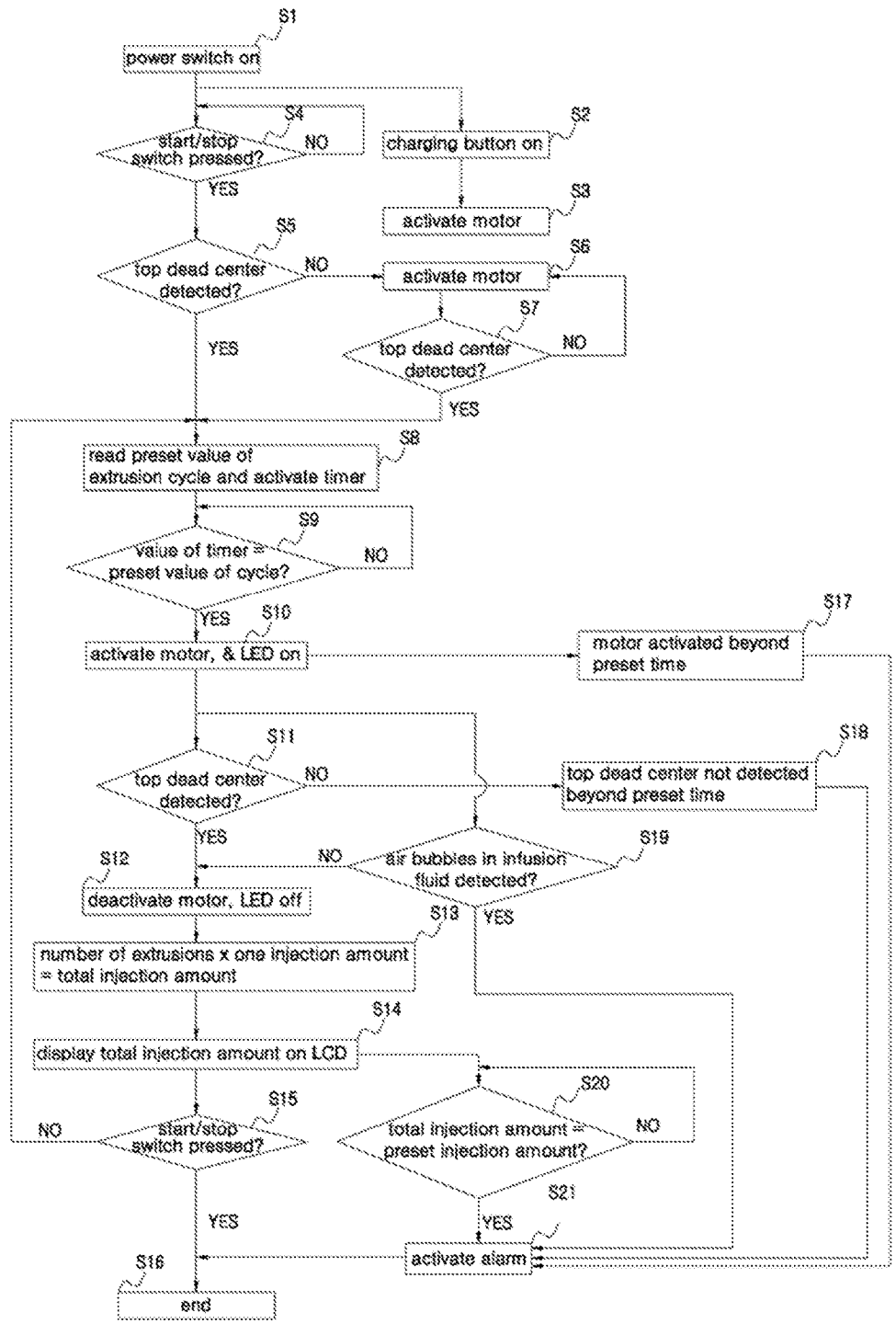
FIG. 20 is a flowchart illustrating an electrical control operation according to the present invention.

The present invention having the above-described functions will be described with reference to FIGS. 19 and 20.

The power switch is turned on (S1). Next, the charging button is turned on (S2) to activate the motor (S3). At this point, the infusion fluid set 11 is charged with an infusion fluid.

Next, the start/stop switch is pressed to start the operation of the device (S4). At this point, the hall sensor 67 detects the top dead center (S5). When the top dead center is not detected, the motor is activated (S6) and then the top dead center is detected again (S7). When the top dead center is detected, a preset value of an extrusion cycle is read and the timer is activated (S8).

When the value of the timer and the preset value of the extrusion cycle agree with each other (S9), the motor is activated and the LED is turned on (S10).

If the motor is continuously activated (S17) even after the preset time passes, or if the top dead center is not detected (S18) even after the preset time passes, or if air bubbles in the infusion fluid are detected by the sound sensor 68 (S19), the alarm is activated (S21) and the operation of the device is finished.

When the motor is normally activated, the LED is turned on (S10), and the top dead center is detected (S11), the motor is deactivated and the LED is turned off (S12). The total amount of injection is calculated by multiplying the amount of injection for one injection by the number of extrusions (S13) and the total amount of injection is displayed on the LCD 65 (S14).

When the start/stop switch is pressed to stop the operation of the device (S15), the operation of the device is stopped (S16). Until the start/stop switch is pressed to stop the operation of the device, the value of the extrusion cycle is continuously read and the timer is activated (S8). When the total amount of injection and the preset amount of injection agree with each other through periodic activation of the motor (S20), the alarm is activated (S21) and the operation is finished.

Industrial Applicability

The intravenous fluid supply device according to the present invention safely and automatically injects a predetermined amount of an infusion fluid at regular time intervals in a manipulated manner using a microprocessor technology.

The present invention offers convenience in use because the intravenous fluid supply device can inject an infusion fluid regardless of whether an infusion fluid storage container (infusion bag) is positioned to be lower or higher than the part (human body) to which an infusion fluid is injected.

Since a geared motor, which is the main driving source of the extrusion means, is not continuously activated but is instantly activated at an inputted repetition cycle, the amount of power consumption is substantially reduced and a small power storage scheme can be applied. In addition, an extrusion means, a control means, and a battery are integrally received in a body, the number of components is minimized and the structure of the device is simplified, thereby enabling compactness of a product, improving portability of a product, and providing the economic merit of low cost.

The intravenous fluid supply device according to the present invention enables day and night visual checking for normal supply of an infusion fluid without using a conventional drop pipette, no matter what position the intravenous fluid supply device is placed, i.e., horizontal, vertical, high, or low. The intravenous fluid supply device according to the present invention guarantees safety by activating an alarm when air is included in an infusion fluid, when an infusion fluid is injected excessively or insufficiently, when a preset total amount of injection is reached, or when a battery voltage is below a preset value.

The invention claimed is:

1. An intravenous fluid supply device, comprising:
   an infusion fluid set configured to be inserted in a space of a body of the intravenous fluid supply device, the infusion fluid set including an elastic tube in which a suction check valve and an extrusion check valve are installed;

a motor mounted on a motor fixing plate;
a cam engaged with the motor and slidably installed in a cam receiving space defined in a cam housing;
an input device that sets an extrusion repetition cycle of the motor and a total injection amount;
a detector including a hall sensor attached to the motor fixing plate, a permanent magnet located in the cam housing in a corresponding position of the hall sensor, and a sound sensor mounted on a main part of the body;
a motor driver for activating the motor to extrude an infusion fluid;
a microcontroller that controls the motor driver according to inputs made by the input device and the detector;
a tension spring elastically installed between a pin fixed to an upper surface of the body and a pin fixed to the cam housing, wherein the cam housing engaged with a shaft and the motor fixing plate engaged with the shaft are interlockingly pivoted and turned so that, when the cam housing is lifted, a state of the lifted cam housing is maintained due to a fly-back action of the tension spring; and
a bolt screwed into the cam housing and protruding toward the upper surface of the body, thereby adjusting an extrusion amount of the infusion fluid by adjusting a gap between a lower surface of the cam housing and the upper surface of the body,
wherein the motor fixing plate has a protruding portion configured to press the elastic tube when the motor is activated.

2. The intravenous fluid supply device according to claim 1, wherein the suction check valve includes:
a suction check valve body that includes an inlet with an end portion provided with an orifice, and a valve seat;
a cap that is inserted in the suction check valve body, has a protrusion pin, and an outlet penetrating the cap; and
a valve plate that is inserted into a space between the valve seat and the cap and is positioned in a center of the valve seat,
wherein the protrusion pin protrudes such that the valve plate comes into contact with the valve seat.

3. The intravenous fluid supply device according to claim 2, wherein the sound sensor detects a sound signal that is generated when an air-mixed infusion fluid flows through the orifice of the suction check valve, and determines whether a loudness level of the sound signal is within a specific band.

4. The intravenous fluid supply device according to claim 2, wherein the extrusion check valve includes:
an extrusion check valve body that includes an inlet and a valve seat;
a cap that is inserted in the extrusion check valve body, has a protrusion pin, and has an orifice formed to be punched in an end portion of an outlet; and
a valve plate that is inserted into a space between the valve seat and the cap and is positioned in the center of the valve seat,
wherein the protrusion pin protrudes such that the valve plate comes into contact with the valve seat.

5. The intravenous fluid supply device according to claim 4, wherein the valve plate of the extrusion check valve is thicker or more rigid than the valve plate of the suction check valve.

6. The intravenous fluid supply device according to claim 4, wherein the sound sensor detects a sound signal generated when an air-mixed infusion fluid flows through the orifice of the extrusion check valve, and determines whether a loudness level of the sound signal is within a specific band.

7. The intravenous fluid supply device according to claim 1, wherein the infusion fluid set further includes a see-through pipe connected to the elastic tube, and
wherein a first buoy having a specific gravity lower than that of the infusion fluid is inserted into an introduction side of the see-through pipe and a second buoy having a specific gravity higher than that of the infusion fluid is inserted into an exit side of the see-through pipe.

8. The intravenous fluid supply device according to claim 1, wherein an excessive injection is prevented by detecting whether activation of the motor continues even after a preset time passes.

9. The intravenous fluid supply device according to claim 1, wherein the motor is activated until the motor fixing plate reaches a top dead center that is detected when the hall sensor approaches the permanent magnet.

10. The intravenous fluid supply device according to claim 1, wherein the input device further comprising:
a repetition cycle setting dial to set the extrusion repetition cycle,
a total injection amount setting dial to set the total injection amount,
an alarm activated to stop operation of the intravenous fluid supply device when the total injection amount that is set by the total injection amount setting dial matches with an actual total injection amount that is calculated by multiplying the number of injections by an amount of injection for a single injection.

* * * * *